United States Patent
Pals et al.

(10) Patent No.: US 9,670,132 B2
(45) Date of Patent: *Jun. 6, 2017

(54) DIBASIC ESTERS AND THE USE THEREOF IN PLASTICIZER COMPOSITIONS

(71) Applicant: Elevance Renewable Sciences, Inc., Woodridge, IL (US)

(72) Inventors: Tessa Pals, Woodridge, IL (US); Steven A. Cohen, Woodridge, IL (US); Thomas E. Snead, Woodridge, IL (US); Allyson Beuhler, Woodridge, IL (US); Paul A. Bertin, Woodridge, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/950,205

(22) Filed: Nov. 24, 2015

(65) Prior Publication Data

US 2016/0152547 A1 Jun. 2, 2016

Related U.S. Application Data

(63) Continuation of application No. 14/644,940, filed on Mar. 11, 2015, now Pat. No. 9,267,013.

(Continued)

(51) Int. Cl.
*C07C 69/67* (2006.01)
*C08K 5/06* (2006.01)
(Continued)

(52) U.S. Cl.
CPC ............. *C07C 69/67* (2013.01); *C07C 69/34* (2013.01); *C08K 5/06* (2013.01); *C08K 5/11* (2013.01)

(58) Field of Classification Search
None
See application file for complete search history.

(56) References Cited

U.S. PATENT DOCUMENTS

| 8,105,970 B2 | 1/2012 | Okada et al. |
| 2009/0214457 A1 | 8/2009 | Dierker et al. |
| 2013/0074931 A1 | 3/2013 | Chen et al. |

FOREIGN PATENT DOCUMENTS

WO 2010/109409 9/2010

OTHER PUBLICATIONS

Database Caplus Chemical Abstracts Service, Columbus, Ohio, US; Database Accession No. 1980:645274, Abstract of JP 55085510, Shiseido Co., Ltd., Japan, Jun. 27, 1980.*

(Continued)

*Primary Examiner* — Karl J Puttlitz
(74) *Attorney, Agent, or Firm* — Kilpatrick Townsend & Stockton LLP

(57) ABSTRACT

Dibasic esters (diesters) and their use in plasticizer compositions are generally disclosed. In some embodiments, the diesters are branched-chain esters of long-chain alkanedioic acids, such as octadecanedioic acid. In some embodiments, such plasticizer compositions are used to increase the plasticity of a polymer resin, such as a vinyl chloride resin or poly vinyl butyral. In some other embodiments, such plasticizer compositions are used to lower the glass transition temperature of a polymer resin. In some embodiments, at least a portion of the plasticizer is derived from a renewable source, such as a natural oil.

9 Claims, 1 Drawing Sheet

Related U.S. Application Data

(60) Provisional application No. 62/048,382, filed on Sep. 10, 2014, provisional application No. 61/954,378, filed on Mar. 17, 2014.

(51) Int. Cl.
*C07C 69/34* (2006.01)
*C08K 5/11* (2006.01)

(56) References Cited

OTHER PUBLICATIONS

Database Caplus Chemical Abstracts Service, Columbus, Ohio, US; Database Accession No. 1964:404716, Abstract of Nieschlag et al., Industrial & Engineering Chemistry Product Research and Development (1964), 3(2), 146-9.*
Database Caplus Chemical Abstracts Service, Columbus, Ohio, US; Database Accession No. 1958:2037, Abstract of GB 775560, Jones, Shiseido Co., Geigy Co., Ltd, May 29, 1957, 2-position.*
Database Caplus Chemical Abstracts Service, Columbus, Ohio, US; Database Accession No. 1990:442816, Abstract of Jayasuriya et al., Journal of the American Chemical Society (1990), 112(15), 5844-50.*
Database Caplus Chemical Abstracts Service, Columbus, Ohio, US; Database Accession No. 2011:481163, Abstract of Xing et al., Polymers for Advanced Technologies (2011), 22(5), 669-674.*
Database Caplus Chemical Abstracts Service, Columbus, Ohio, US; Database Accession No. 1958:2037, Abstract of GB 775560, Jones, Shiseido Co., Geigy Co., Ltd, May 29, 1957, 3-position.*
Database Caplus Chemical Abstracts Service, Columbus, Ohio, US; Database Accession No. 1970:6415, Abstract of Schlenk et al., Justus Liebigs Annalen der Chemie (1969), 727, 1-9.*
International Search Report, PCT Application No. PCT/US15/019935, dated Apr. 16, 2015.
Stark et al, Geosynthetics Int'l, vol. 12, pp. 1-12 (2005).
Stark et al., Proc. of Canadian Geotechnical Conf., Session 5D, pp. 1-7 (2004).
Navarro et al., Macromolecules, vol. 32, pp. 2377-2381 (2010).
Mao et al., Proc. of Int'l Conf. on Life Science and Eng., pp. 43-48 (2012).

* cited by examiner

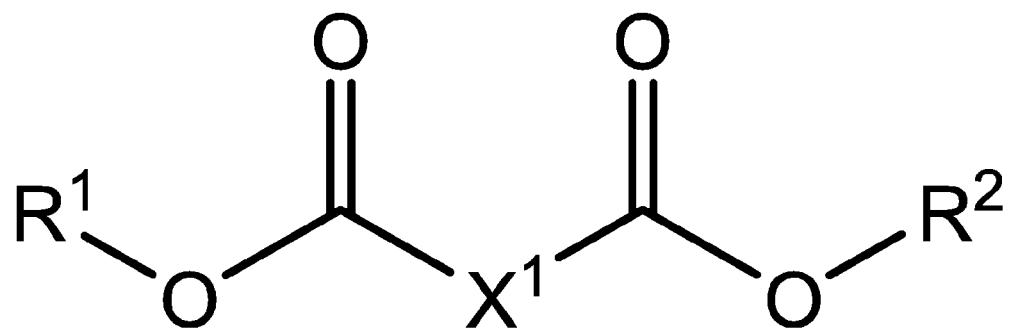

DIBASIC ESTERS AND THE USE THEREOF IN PLASTICIZER COMPOSITIONS

CROSS-REFERENCE TO RELATED APPLICATIONS

The present application is a continuation application of U.S. patent application Ser. No. 14/644,940, filed on Mar. 11, 2015, which claims the benefit of priority of U.S. Provisional Application Nos. 61/954,378, filed Mar. 17, 2014; and 62/048,382, filed Sep. 10, 2014. The aforementioned priority applications are hereby incorporated by reference as though fully set forth herein in their entirety.

TECHNICAL FIELD

Dibasic esters (diesters) and their use in plasticizer compositions are generally disclosed. In some embodiments, the diesters are branched-chain esters of long-chain alkanedioic acids, such as octadecanedioic acid. In some embodiments, such plasticizer compositions are used to increase the plasticity of a polymer resin, such as a vinyl chloride resin or poly vinyl butyral. In some other embodiments, such plasticizer compositions are used to lower the glass transition temperature of a polymer resin. In some embodiments, at least a portion of the plasticizer is derived from a renewable source, such as a natural oil.

BACKGROUND

It can often be desirable to modify the properties of a polymer resin through the addition of certain additives. Plasticizers are one such class of additives that can be added to a polymer resin to change certain properties of the resulting composition. These changes in properties include lowering the glass transition temperature of the resin, increasing the plasticity (e.g., flowability) of the resin, and the like.

Inclusion of plasticizers into polymer compositions is not without its problems, however. For example, plasticizer compounds can often migrate within the composition and migrate to the surface or to boundaries (e.g., boundaries in a laminate). Therefore, there is a continuing need to develop new plasticizer compounds and compositions, where the plasticizer compounds are less susceptible to migration within the polymer.

SUMMARY

In a first aspect, the disclosure provides compounds of formula (I):

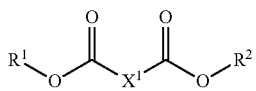

(I)

wherein: $X^1$ is $C_{11-24}$ alkylene or $C_{11-24}$ alkenylene, each of which is optionally substituted by one or more substituents selected independently from $R^3$; $R^1$ is a branched or unbranched $C_{4-24}$ alkyl, a branched or unbranched $C_{4-24}$ alkenyl, a branched or unbranched $C_{4-30}$ oxyalkyl, or a branched or unbranched $C_{4-30}$ oxyalkenyl, each of which is optionally substituted by one or more substituents selected independently from $R^3$; $R^2$ is a branched or unbranched $C_{4-24}$ alkyl, a branched or unbranched $C_{4-24}$ alkenyl, a branched or unbranched $C_{4-30}$ oxyalkyl, or a branched or unbranched $C_{4-30}$ oxyalkenyl, each of which is optionally substituted by one or more substituents selected independently from $R^3$; and $R^3$ is a halogen atom, —OH, —NH$_2$, $C_{1-6}$ alkyl, $C_{1-6}$ heteroalkyl, $C_{2-6}$ alkenyl, or $C_{2-6}$ heteroalkenyl.

In some embodiments of the first aspect, $X^1$ is $C_{11-24}$ alkylene or $C_{11-24}$ alkenylene, each of which is optionally substituted by one or more substituents selected independently from $R^3$; $R^1$ is a branched $C_{4-20}$ alkyl, a branched $C_{4-20}$ alkenyl, a branched $C_{4-20}$ oxyalkyl, or a branched $C_{4-20}$ oxyalkenyl, each of which is optionally substituted by one or more substituents selected independently from $R^3$; $R^2$ is a branched $C_{4-20}$ alkyl, a branched $C_{4-20}$ alkenyl, a branched $C_{4-20}$ oxyalkyl, or a branched $C_{4-20}$ oxyalkenyl, each of which is optionally substituted by one or more substituents selected independently from $R^3$; and $R^3$ is a halogen atom, —OH, —NH$_2$, $C_{1-6}$ alkyl, $C_{1-6}$ heteroalkyl, $C_{2-6}$ alkenyl, or $C_{2-6}$ heteroalkenyl.

In a second aspect, the disclosure provides plasticizer compositions, including a compound of formula (II):

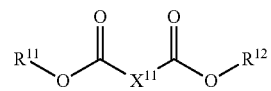

(II)

wherein: $X^{11}$ is $C_{11-24}$ alkylene or $C_{11-24}$ alkenylene, each of which is optionally substituted by one or more substituents selected independently from $R^{13}$; $R^{11}$ is a branched or unbranched $C_{4-20}$ alkyl, a branched or unbranched $C_{4-20}$ alkenyl, a branched or unbranched $C_{4-20}$ oxyalkyl, or a branched or unbranched $C_{4-20}$ oxyalkenyl, each of which is optionally substituted by one or more substituents selected independently from $R^{13}$; $R^{12}$ is a branched or unbranched $C_{4-20}$ alkyl, a branched or unbranched $C_{4-20}$ alkenyl, a branched or unbranched $C_{4-20}$ oxyalkyl, or a branched or unbranched $C_{4-20}$ oxyalkenyl, each of which is optionally substituted by one or more substituents selected independently from $R^{13}$; and $R^{13}$ is a halogen atom, —OH, —NH$_2$, $C_{1-6}$ alkyl, $C_{1-6}$ heteroalkyl, $C_{2-6}$ alkenyl, or $C_{2-6}$ heteroalkenyl.

In a third aspect, the disclosure provides polymer compositions comprising: a polymeric resin and a plasticizer composition of the second aspect.

In a fourth aspect, the disclosure provides methods of increasing the plasticity of a polymeric resin, including: providing a polymeric resin; and contacting the polymeric resin with the plasticizer composition of the second aspect.

In a fifth aspect, the disclosure provides methods of lowering the glass transition temperature ($T_g$) of a polymeric resin, including: providing a polymeric resin; and contacting the polymeric resin with the plasticizer composition of the second aspect.

In a sixth aspect, the disclosure provides a laminated article, comprising: a first transparent layer; and a second transparent layer disposed on the first transparent layer, the second transparent layer comprising a polymer composition of the third aspect. In some embodiments, the first transparent layer is a glass sheet. In some further embodiments, the laminated article includes a third transparent layer disposed on the second transparent layer opposite the first transparent layer. In some such embodiments, the third transparent layer is a glass sheet.

In a seventh aspect, the disclosure provides a laminated article, comprising: a first transparent layer having a photovoltaic cell (or a portion of a photovoltaic cell) disposed thereon; and a second transparent layer disposed on the first transparent layer, the second transparent layer comprising a polymer composition of the third aspect. In some embodiments, the first transparent layer is a glass sheet. In some further embodiments, the laminated article includes a third transparent layer disposed on the second transparent layer opposite the first transparent layer. In some such embodiments, the third transparent layer is a glass sheet.

In a eighth aspect, the disclosure provides a laminated article, comprising: a first transparent layer; and a second transparent layer disposed on the first transparent layer, the second transparent layer comprising a polymer composition of the third aspect and one or more electrochromic materials. In some embodiments, the first transparent layer is a glass sheet. In some further embodiments, the laminated article includes a third transparent layer disposed on the second transparent layer opposite the first transparent layer. In some such embodiments, the third transparent layer is a glass sheet.

Further aspects and embodiments are provided in the foregoing drawings, detailed description and claims.

BRIEF DESCRIPTION OF THE DRAWINGS

The following drawings are provided for purposes of illustrating various embodiments of the compositions and methods disclosed herein. The drawings are provided for illustrative purposes only, and are not intended to describe any preferred compositions or preferred methods, or to serve as a source of any limitations on the scope of the claimed inventions.

FIG. 1 shows a non-limiting example of a compound of certain embodiments disclosed herein, wherein: $X^1$ is $C_{11-24}$ alkylene or $C_{11-24}$ alkenylene, each of which is optionally substituted; $R^1$ is a branched or unbranched $C_{4-24}$ alkyl, a branched or unbranched $C_{4-24}$ alkenyl, a branched or unbranched $C_{4-24}$ oxyalkyl, or a branched or unbranched $C_{4-30}$ oxyalkenyl, each of which is optionally substituted; $R^2$ is a branched or unbranched $C_{4-24}$ alkyl, a branched or unbranched $C_{4-24}$ alkenyl, a branched or unbranched $C_{4-30}$ oxyalkyl, or a branched or unbranched $C_{4-30}$ oxyalkenyl, each of which is optionally substituted.

DETAILED DESCRIPTION

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "polymer" refers to a substance having a chemical structure that includes the multiple repetition of constitutional units formed from substances of comparatively low relative molecular mass relative to the molecular mass of the polymer. The term "polymer" includes soluble and/or fusible molecules having chains of repeat units, and also includes insoluble and infusible networks. As used herein, the term "polymer" can include oligomeric materials, which have only a few (e.g., 5-100) constitutional units As used herein, "monomer" refers to a substance that can undergo a polymerization reaction to contribute constitutional units to the chemical structure of a polymer.

As used herein, "copolymer" refers to a polymer having constitutional units formed from more than one species of monomer.

As used herein, "natural oil," "natural feedstock," or "natural oil feedstock" refer to oils derived from plants or animal sources. These terms include natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

As used herein, "natural oil derivatives" refers to the compounds or mixtures of compounds derived from a natural oil using any one or combination of methods known in the art. Such methods include but are not limited to saponification, fat splitting, transesterification, esterification, hydrogenation (partial, selective, or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil). Soybean oil typically comprises about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9, 12-octadecadienoic acid), and linolenic acid (9,12,15-octadecatrienoic acid).

As used herein, "metathesis catalyst" includes any catalyst or catalyst system that catalyzes an olefin metathesis reaction.

As used herein, "metathesize" or "metathesizing" refer to the reacting of a feedstock in the presence of a metathesis catalyst to form a "metathesized product" comprising new olefinic compounds, i.e., "metathesized" compounds. Metathesizing is not limited to any particular type of olefin metathesis, and may refer to cross-metathesis (i.e., co-metathesis), self-metathesis, ring-opening metathesis, ring-opening metathesis polymerizations ("ROMP"), ring-closing metathesis ("RCM"), and acyclic diene metathesis ("ADMET"). In some embodiments, metathesizing refers to reacting two triglycerides present in a natural feedstock (self-metathesis) in the presence of a metathesis catalyst, wherein each triglyceride has an unsaturated carbon-carbon double bond, thereby forming a new mixture of olefins and esters which may include a triglyceride dimer. Such triglyceride dimers may have more than one olefinic bond, thus higher oligomers also may form. Additionally, in some other embodiments, metathesizing may refer to reacting an olefin, such as ethylene, and a triglyceride in a natural feedstock having at least one unsaturated carbon-carbon double bond, thereby forming new olefinic molecules as well as new ester molecules (cross-metathesis).

As used herein, "hydrocarbon" refers to an organic group composed of carbon and hydrogen, which can be saturated or unsaturated, and can include aromatic groups. The term "hydrocarbyl" refers to a monovalent or polyvalent hydrocarbon moiety.

As used herein, "olefin" or "olefins" refer to compounds having at least one unsaturated carbon-carbon double bond. In certain embodiments, the term "olefins" refers to a group of unsaturated carbon-carbon double bond compounds with different carbon lengths. Unless noted otherwise, the terms "olefin" or "olefins" encompasses "polyunsaturated olefins" or "poly-olefins," which have more than one carbon-carbon double bond. As used herein, the term "monounsaturated olefins" or "mono-olefins" refers to compounds having only one carbon-carbon double bond. A compound having a terminal carbon-carbon double bond can be referred to as a "terminal olefin" or an "alpha-olefin," while an olefin having a non-terminal carbon-carbon double bond can be referred to as an "internal olefin." In some embodiments, the alpha-olefin is a terminal alkene, which is an alkene (as defined below) having a terminal carbon-carbon double bond. Additional carbon-carbon double bonds can be present.

The number of carbon atoms in any group or compound can be represented by the terms: "$C_z$", which refers to a group of compound having z carbon atoms; and "$C_{x-y}$", which refers to a group or compound containing from x to y, inclusive, carbon atoms. For example, "$C_{1-6}$ alkyl" represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. As a further example, a "$C_{4-10}$ alkene" refers to an alkene molecule having from 4 to 10 carbon atoms, and, for example, includes, but is not limited to, 1-butene, 2-butene, isobutene, 1-pentene, 1-hexene, 3-hexene, 1-heptene, 3-heptene, 1-octene, 4-octene, 1-nonene, 4-nonene, and 1-decene.

As used herein, the term "low-molecular-weight olefin" may refer to any one or combination of unsaturated straight, branched, or cyclic hydrocarbons in the $C_{2-14}$ range. Low-molecular-weight olefins include alpha-olefins, wherein the unsaturated carbon-carbon bond is present at one end of the compound. Low-molecular-weight olefins may also include dienes or trienes. Low-molecular-weight olefins may also include internal olefins or "low-molecular-weight internal olefins." In certain embodiments, the low-molecular-weight internal olefin is in the $C_{4-14}$ range. Examples of low-molecular-weight olefins in the $C_{2-6}$ range include, but are not limited to: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Non-limiting examples of low-molecular-weight olefins in the $C_{7-9}$ range include 1,4-heptadiene, 1-heptene, 3,6-nonadiene, 3-nonene, 1,4,7-octatriene. Other possible low-molecular-weight olefins include styrene and vinyl cyclohexane. In certain embodiments, it is preferable to use a mixture of olefins, the mixture comprising linear and branched low-molecular-weight olefins in the $C_{4-10}$ range. Olefins in the $C_{4-10}$ range can also be referred to as "short-chain olefins," which can be either branched or unbranched. In one embodiments, it may be preferable to use a mixture of linear and branched $C_4$ olefins (i.e., combinations of: 1-butene, 2-butene, and/or isobutene). In other embodiments, a higher range of $C_{11-14}$ may be used.

In some instances, the olefin can be an "alkene," which refers to a straight- or branched-chain non-aromatic hydrocarbon having 2 to 30 carbon atoms and one or more carbon-carbon double bonds, which may be optionally substituted, as herein further described, with multiple degrees of substitution being allowed. A "monounsaturated alkene" refers to an alkene having one carbon-carbon double bond, while a "polyunsaturated alkene" refers to an alkene having two or more carbon-carbon double bonds. A "lower alkene," as used herein, refers to an alkene having from 2 to 10 carbon atoms.

As used herein, "ester" or "esters" refer to compounds having the general formula: R—COO—R', wherein R and R' denote any organic group (such as alkyl, aryl, or silyl groups) including those bearing heteroatom-containing substituent groups. In certain embodiments, R and R' denote alkyl, alkenyl, aryl, or alcohol groups. In certain embodiments, the term "esters" may refer to a group of compounds with the general formula described above, wherein the compounds have different carbon lengths. In certain embodiments, the esters may be esters of glycerol, which is a trihydric alcohol. The term "glyceride" can refer to esters where one, two, or three of the —OH groups of the glycerol have been esterified.

It is noted that an olefin may also comprise an ester, and an ester may also comprise an olefin, if the R or R' group in the general formula R—COO—R' contains an unsaturated carbon-carbon double bond. Such compounds can be referred to as "unsaturated esters" or "olefin ester" or "olefinic ester compounds." Further, a "terminal olefinic ester compound" may refer to an ester compound where R has an olefin positioned at the end of the chain. An "internal olefin ester" may refer to an ester compound where R has an olefin positioned at an internal location on the chain. Additionally, the term "terminal olefin" may refer to an ester or an acid thereof where R' denotes hydrogen or any organic compound (such as an alkyl, aryl, or silyl group) and R has an olefin positioned at the end of the chain, and the term "internal olefin" may refer to an ester or an acid thereof where R' denotes hydrogen or any organic compound (such as an alkyl, aryl, or silyl group) and R has an olefin positioned at an internal location on the chain.

As used herein, "acid," "acids," "carboxylic acid," or "carboxylic acids" refer to compounds having the general formula: R—COOH, wherein R denotes any organic moiety (such as alkyl, aryl, or silyl groups), including those bearing heteroatom-containing substituent groups. In certain embodiments, R denotes alkyl, alkenyl, aryl, or alcohol groups. In certain embodiments, the term "acids" or "carboxylic acids" may refer to a group of compounds with the general formula described above, wherein the compounds have different carbon lengths.

As used herein, "alcohol" or "alcohols" refer to compounds having the general formula: R—OH, wherein R denotes any organic moiety (such as alkyl, aryl, or silyl groups), including those bearing heteroatom-containing substituent groups. In certain embodiments, R denotes alkyl, alkenyl, aryl, or alcohol groups. In certain embodiments, the term "alcohol" or "alcohols" may refer to a group of compounds with the general formula described above, wherein the compounds have different carbon lengths. As used herein, the term "alkanol" refers to alcohols where R is an alkyl group.

As used herein, "alkyl" refers to a straight or branched chain saturated hydrocarbon having 1 to 30 carbon atoms, which may be optionally substituted, as herein further described, with multiple degrees of substitution being allowed. Examples of "alkyl," as used herein, include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl. The number of carbon atoms in an alkyl group is represented by the phrase "$C_{x-y}$ alkyl," which refers to an alkyl group, as herein defined, containing from x to y, inclusive, carbon atoms. Thus, "$C_{1-6}$ alkyl" represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. In some instances, the "alkyl" group can be divalent, in which case the group can alternatively be referred to as an "alkylene" group. Also, in some instances, one or more of the carbon atoms in the alkyl or alkylene group can be replaced by a heteroatom (e.g., selected from nitrogen, oxygen, or sulfur, including N-oxides, sulfur oxides, and sulfur dioxides, where feasible), and is referred to as a "heteroalkyl" or "heteroalkylene" group, respectively. Non-limiting examples include "oxyalkyl" or "oxyalkylene" groups, which are groups of the following formulas: -[-(alkylene)-O-]$_x$-alkyl, or -[-(alkylene)-O-]$_x$-alkylene-, respectively, where x is 1 or more, such as 1, 2, 3, 4, 5, 6, 7, or 8.

As used herein, "alkenyl" refers to a straight or branched chain non-aromatic hydrocarbon having 2 to 30 carbon atoms and having one or more carbon-carbon double bonds, which may be optionally substituted, as herein further described, with multiple degrees of substitution being allowed. Examples of "alkenyl," as used herein, include, but are not limited to, ethenyl, 2-propenyl, 2-butenyl, and 3-butenyl. The number of carbon atoms in an alkenyl group is represented by the phrase "$C_{x-y}$ alkenyl," which refers to an alkenyl group, as herein defined, containing from x to y, inclusive, carbon atoms. Thus, "$C_{2-6}$ alkenyl" represents an alkenyl chain having from 2 to 6 carbon atoms and, for example, includes, but is not limited to, ethenyl, 2-propenyl, 2-butenyl, and 3-butenyl. In some instances, the "alkenyl" group can be divalent, in which case the group can alternatively be referred to as an "alkenylene" group. Also, in some instances, one or more of the saturated carbon atoms in the alkenyl or alkenylene group can be replaced by a heteroatom (e.g., selected from nitrogen, oxygen, or sulfur, including N-oxides, sulfur oxides, and sulfur dioxides, where feasible), and is referred to as a "heteroalkenyl" or "heteroalkenylene" group, respectively. Non-limiting examples include "oxyalkenyl" or "oxyalkenylene" groups, which are groups of the following formulas: —[—($R^f$)—O—]$_x$—$R^g$, or —[—($R^f$)—O—]$_x$—$R^h$—, respectively, where x is 1 or more, such as 1, 2, 3, 4, 5, 6, 7, or 8, and $R^f$, $R^g$, and $R^h$ are independently alkyl/alkylene or alkenyl/alkenylene groups, provided that each such "oxyalkenyl" or "oxyalkenylene" group contains at least one carbon-carbon double bond.

As used herein, the term "branched," for example, in reference to an alkyl or alkenyl group, refers to the presence of one or more carbon atoms having three or four connections to other carbon atoms. By contrast, the term "unbranched" refers to groups not having any carbon atoms with three or four connections to other carbon atoms. For example, groups such as isopropyl, isobutyl, sec-butyl, and tert-butyl are branched, and groups such as n-propyl and n-butyl are unbranched. In some instances, it may be desirable to refer to a position for the branching, such as in the alcoholic portion of an ester. In such instances, the carbon atom immediately adjacent to the oxygen atom on the alcoholic side of the ester is the 1-position, the next in the 2-position, and so on. Thus, the alkyl group of sec-butyl alcohol or isopropyl alcohol is said to be branched at the 1-position, and the alkyl group of isobutyl alcohol is said to be branched at the 2-position and not branched at the 1-position, and so forth. The same principles apply to alkenyl groups, as the double bond does not count as 2 connections. Thus, groups like 9-octedenenyl are said to be unbranched, while a group like 1-methyl-9-octadenenyl is said to be branched, i.e., at the 1-position.

As used herein, "halogen" or "halo" refers to a fluorine, chlorine, bromine, and/or iodine atom. In some embodiments, the terms refer to fluorine and/or chlorine.

As used herein, "substituted" refers to substitution of one or more hydrogen atoms of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week. As used herein, the phrases "substituted with one or more . . . " or "substituted one or more times . . . " refer to a number of substituents that equals from one to the maximum number of substituents possible based on the number of available bonding sites, provided that the above conditions of stability and chemical feasibility are met.

As used herein, "mix" or "mixed" or "mixture" refers broadly to any combining of two or more compositions. The two or more compositions need not have the same physical state; thus, solids can be "mixed" with liquids, e.g., to form a slurry, suspension, or solution. Further, these terms do not require any degree of homogeneity or uniformity of composition. This, such "mixtures" can be homogeneous or heterogeneous, or can be uniform or non-uniform. Further, the terms do not require the use of any particular equipment to carry out the mixing, such as an industrial mixer.

As used herein, "optionally" means that the subsequently described event(s) may or may not occur. In some embodiments, the optional event does not occur. In some other embodiments, the optional event does occur one or more times.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., $A_1$ and $A_2$, then one or more members of the class can be present concurrently.

As used herein, the various functional groups represented will be understood to have a point of attachment at the functional group having the hyphen or dash (-) or an asterisk (*). In other words, in the case of —CH$_2$CH$_2$CH$_3$, it will be understood that the point of attachment is the CH$_2$ group at the far left. If a group is recited without an asterisk or a dash, then the attachment point is indicated by the plain and ordinary meaning of the recited group.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

Other terms are defined in other portions of this description, even though not included in this subsection.

Branched-Chain Diesters of Alkanedioic Acids and Alkenedioic Acids

In certain aspects, the disclosure provides compounds that are branched-chain diesters (i.e., formed from branched-chain alcohols) of alkanedioic acids and/or alkenedioic acids, wherein the alkanedioic acids and/or alkenedioic acids have at least 13 carbon atoms, or at least 14 carbon atoms, or at least 16 carbon atoms, up to 24 carbon atoms. In some embodiments the alkanedioic acids and/or alkenedioic acids have 18 carbon atoms, such as octadecanedioic acid, 9-octadecenedioic acid, and the like.

In some embodiments, the branched-chain diesters are compounds of formula (I):

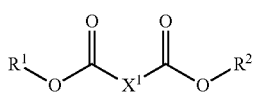

(I)

wherein: $X^1$ is $C_{11-24}$ alkylene or $C_{11-24}$ alkenylene, each of which is optionally substituted by one or more substituents selected independently from $R^3$; $R^1$ is a branched or unbranched $C_{4-24}$ alkyl, a branched or unbranched $C_{4-24}$ alkenyl, a branched or unbranched $C_{4-30}$ oxyalkyl, or a branched or unbranched $C_{4-30}$ oxyalkenyl, each of which is optionally substituted by one or more substituents selected independently from $R^3$; $R^2$ is a branched or unbranched $C_{4-24}$ alkyl, a branched or unbranched $C_{4-24}$ alkenyl, a branched or unbranched $C_{4-30}$ oxyalkyl, or a branched or unbranched $C_{4-30}$ oxyalkenyl, each of which is optionally substituted by one or more substituents selected independently from $R^3$; and $R^3$ is a halogen atom, —OH, —NH$_2$, $C_{1-6}$ alkyl, $C_{1-6}$ heteroalkyl, $C_{2-6}$ alkenyl, or $C_{2-6}$ heteroalkenyl.

In some embodiments, $X^1$ is $C_{11-24}$ alkylene, optionally substituted one or more times with substituents selected independently from —OH and $C_{1-6}$ alkyloxy. In some embodiments, $X^1$ is $C_{12-24}$ alkylene, optionally substituted one or more times with substituents selected independently from —OH and $C_{1-6}$ alkyloxy. In some embodiments, $X^1$ is $C_{12-20}$ alkylene, optionally substituted one or more times with substituents selected independently from —OH and $C_{1-6}$ alkyloxy. In some embodiments, $X^1$ is $C_{14-20}$ alkylene, optionally substituted one or more times with substituents selected independently from —OH and $C_{1-6}$ alkyloxy. In some embodiments, $X^1$ is $C_{14-18}$ alkylene, optionally substituted one or more times with substituents selected independently from —OH and $C_{1-6}$ alkyloxy. In some embodiments, $X^1$ is $C_{16}$ alkylene, optionally substituted one or more times with substituents selected independently from —OH and $C_{1-6}$ alkyloxy. In some embodiments, $X^1$ is —(CH$_2$)$_{12}$—, —(CH$_2$)$_{14}$—, —(CH$_2$)$_{16}$—, —(CH$_2$)$_{18}$—, —(CH$_2$)$_{20}$—, or —(CH$_2$)$_{22}$—. In some such embodiments, $X^1$ is —(CH$_2$)$_{14}$—, —(CH$_2$)$_{16}$—, or —(CH$_2$)$_{20}$—. In some embodiments, $X^1$ is —(CH$_2$)$_{16}$—.

In some embodiments, $X^1$ is $C_{11-24}$ alkenylene, optionally substituted one or more times with substituents selected independently from —OH and $C_{1-6}$ alkyloxy. In some embodiments, $X^1$ is $C_{12-24}$ alkenylene, optionally substituted one or more times with substituents selected independently from —OH and $C_{1-6}$ alkyloxy. In some embodiments, $X^1$ is $C_{12-20}$ alkenylene, optionally substituted one or more times with substituents selected independently from —OH and $C_{1-6}$ alkyloxy. In some embodiments, $X^1$ is $C_{14-20}$ alkenylene, optionally substituted one or more times with substituents selected independently from —OH and $C_{1-6}$ alkyloxy. In some embodiments, $X^1$ is $C_{14-18}$ alkenylene, optionally substituted one or more times with substituents selected independently from —OH and $C_{1-6}$ alkyloxy. In some embodiments, $X^1$ is $C_{16}$ alkenylene, optionally substituted one or more times with substituents selected independently from —OH and $C_{1-6}$ alkyloxy. In some embodiments, $X^1$ is —(CH$_2$)$_7$—CH=CH—(CH$_2$)$_7$—. In some other embodiments, $X^1$ is —(CH$_2$)$_5$—CH=CH—(CH$_2$)$_5$—. In some other embodiments, $X^1$ is —(CH$_2$)$_9$—CH=CH—(CH$_2$)$_9$—.

In certain further embodiments of any of the above embodiments, $R^1$ is an unbranched $C_{4-24}$, which is optionally substituted by one or more substituents selected independently from $R^3$. In some further embodiments, $R^1$ is an unbranched $C_{4-20}$ alkyl, which is optionally substituted by one or more substituents selected independently from —OH and $C_{1-6}$ alkyloxy. In some embodiments, $R^1$ is butyl, pentyl, hexyl, heptyl, or octyl.

In some embodiments, $R^1$ is a branched $C_{4-24}$ alkyl, which is optionally substituted by one or more substituents selected independently from $R^3$. In some further embodiments, $R^1$ is a branched $C_{4-20}$ alkyl, which comprises branching at the 1-position of the alkyl moiety, and which is optionally substituted by one or more substituents selected independently from —OH and $C_{1-6}$ alkyloxy. In some embodiments, $R^1$ is a branched $C_{4-20}$ alkyl, which comprises branching at the 2-position of the alkyl moiety, and which is optionally substituted by one or more substituents selected independently from —OH and $C_{1-6}$ alkyloxy. In some embodiments, $R^1$ is a branched $C_{4-20}$ alkyl, which comprises branching at the 3-position of the alkyl moiety, and which is optionally substituted by one or more substituents selected independently from —OH and $C_{1-6}$ alkyloxy. In some embodiments, $R^1$ is a branched $C_{4-20}$ alkyl, which has no branching at the 1-position of the alkyl moiety, and which is optionally substituted by one or more substituents selected independently from —OH and $C_{1-6}$ alkyloxy. In some embodiments, $R^1$ is 2-methylpentyl, 2-ethylhexyl, 2-butyloctyl, and 3-methylbutyl.

In some embodiments, $R^1$ is $C_{4-30}$ oxyalkyl, which is optionally substituted by one or more substituents selected independently from —OH and $C_{1-6}$ alkyloxy. In some embodiments, $R^1$ is $C_{4-24}$ oxyalkyl, which is optionally substituted by one or more substituents selected independently from —OH and $C_{1-6}$ alkyloxy. In some embodiments, $R^1$ is —(CH$_2$—CH$_2$—O)$_{1-14}$—R$^x$, or —(CH$_2$—CH$_2$—O)$_{1-12}$—R$^x$, where R$^x$ is $C_{1-6}$ unbranched alkyl. In some embodiments, R$^x$ is methyl. In some other embodiments, R$^x$ is ethyl. In some embodiments, $R^1$ is —CH$_2$—CH$_2$—O—CH$_3$. In some embodiments, $R^1$ is —(CH$_2$—CH$_2$—O)$_2$—CH$_3$. In some embodiments, $R^1$ is —(CH$_2$—CH$_2$—O)$_3$—CH$_3$. In some embodiments, $R^1$ is —(CH$_2$—CH$_2$—O)$_4$—CH$_3$. In some embodiments, $R^1$ is —(CH$_2$—CH$_2$—O)$_5$—CH$_3$. In some embodiments, $R^1$ is —(CH$_2$—CH$_2$—O)$_6$—CH$_3$. In some embodiments, $R^1$ is —(CH$_2$—CH$_2$—O)$_7$—CH$_3$. In some embodiments, $R^1$ is —(CH$_2$—CH$_2$—O)$_8$—CH$_3$. In some embodiments, $R^1$ is —(CH$_2$—CH$_2$—O)$_9$—CH$_3$. In some embodiments, $R^1$ is —(CH$_2$—CH$_2$—O)$_{10}$—CH$_3$. In some embodiments, $R^1$ is —(CH$_2$—CH$_2$—O)$_{11}$—CH$_3$. In some embodiments, $R^1$ is —(CH$_2$—CH$_2$—O)$_{12}$—CH$_3$.

In certain further embodiments of any of the above embodiments, $R^2$ is an unbranched $C_{4-24}$, which is optionally substituted by one or more substituents selected independently from $R^3$. In some further embodiments, $R^2$ is an unbranched $C_{4-20}$ alkyl, which is optionally substituted by one or more substituents selected independently from —OH and $C_{1-6}$ alkyloxy. In some embodiments, $R^2$ is butyl, pentyl, hexyl, heptyl, or octyl.

In some embodiments, $R^2$ is a branched $C_{4-24}$ alkyl, which is optionally substituted by one or more substituents selected independently from $R^3$. In some further embodiments, $R^2$ is a branched $C_{4-20}$ alkyl, which comprises branching at the 1-position of the alkyl moiety, and which is optionally substituted by one or more substituents selected independently from —OH and $C_{1-6}$ alkyloxy. In some embodiments, $R^2$ is a branched $C_{4-20}$ alkyl, which comprises branching at the 2-position of the alkyl moiety, and which is optionally substituted by one or more substituents selected independently from —OH and $C_{1-6}$ alkyloxy. In some embodiments, $R^2$ is a branched $C_{4-20}$ alkyl, which comprises branching at the 3-position of the alkyl moiety, and which is optionally substituted by one or more substituents selected independently from —OH and $C_{1-6}$ alkyloxy. In some embodiments, $R^2$ is a branched $C_{4-20}$ alkyl, which has no branching at the 1-position of the alkyl moiety, and which is optionally substituted by one or more substituents selected independently from —OH and $C_{1-6}$ alkyloxy. In some embodiments, $R^2$ is 2-methylpentyl, 2-ethylhexyl, 2-butyloctyl, and 3-methylbutyl.

In some embodiments, $R^2$ is $C_{4-30}$ oxyalkyl, which is optionally substituted by one or more substituents selected independently from —OH and $C_{1-6}$ alkyloxy. In some embodiments, $R^2$ is $C_{4-24}$ oxyalkyl, which is optionally substituted by one or more substituents selected independently from —OH and $C_{1-6}$ alkyloxy. In some embodiments, $R^2$ is —(CH$_2$—CH$_2$—O)$_{1-14}$—R$^{x'}$ or —(CH$_2$—CH$_2$—O)$_{1-12}$—R$^{x'}$, where R$^{x'}$ is $C_{1-6}$ unbranched alkyl. In some embodiments, R$^{x'}$ is methyl. In some other embodiments, R$^{x'}$ is ethyl. In some embodiments, $R^2$ is —CH$_2$—CH$_2$—O—CH$_3$. In some embodiments, $R^2$ is —(CH$_2$—CH$_2$—O)$_2$—CH$_3$. In some embodiments, $R^2$ is —(CH$_2$—CH$_2$—O)$_3$—CH$_3$. In some embodiments, $R^2$ is —(CH$_2$—CH$_2$—O)$_4$—CH$_3$. In some embodiments, $R^2$ is —(CH$_2$—CH$_2$—O)$_5$—CH$_3$. In some embodiments, $R^2$ is —(CH$_2$—CH$_2$—O)$_6$—CH$_3$. In some embodiments, $R^2$ is —(CH$_2$—CH$_2$—O)$_7$—CH$_3$. In some embodiments, $R^2$ is —(CH$_2$—CH$_2$—O)$_8$—CH$_3$. In some embodiments, $R^2$ is —(CH$_2$—CH$_2$—O)$_9$—CH$_3$. In some embodiments, $R^2$ is —(CH$_2$—CH$_2$—O)$_{10}$—CH$_3$. In some embodiments, $R^2$ is —(CH$_2$—CH$_2$—O)$_{11}$—CH$_3$. In some embodiments, $R^2$ is —(CH$_2$—CH$_2$—O)$_{12}$—CH$_3$.

In some embodiments of any of the above embodiments, $R^1$ and $R^2$ are the same. In some other embodiments, $R^1$ and $R^2$ are not the same.

The compounds disclosed above are not limited to any particular use or application. In some embodiments, they can be suitable for use as plasticizers, e.g., for polymer resins. They can be suitable for other uses as well.

Plasticizer Compositions

In certain aspects, the disclosure provides plasticizer compositions that include diester compounds. In some embodiments, at least one portion (e.g., the acid portion, one or both alcohol portions, or both the acid portion and one or both alcohol portions) is branched. In some embodiments, the diester compounds are branched-chain diesters (i.e., formed from branched-chain alcohols) of alkanedioic acids and/or alkenedioic acids, wherein the alkanedioic acids and/or alkenedioic acids have at least 13 carbon atoms, or at least 14 carbon atoms, or at least 16 carbon atoms, up to 24 carbon atoms. In some embodiments the alkanedioic acids and/or alkenedioic acids have 18 carbon atoms, such as octadecanedioic acid, 9-octadecenedioic acid, and the like.

In some embodiments, the plasticizer compositions, include a compound of formula (II):

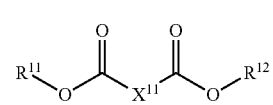

(II)

wherein: $X^{11}$ is $C_{11-24}$ alkylene or $C_{11-24}$ alkenylene, each of which is optionally substituted by one or more substituents selected independently from $R^{13}$; $R^{11}$ is a branched or unbranched $C_{4-24}$ alkyl, a branched or unbranched $C_{4-24}$ alkenyl, a branched or unbranched $C_{4-30}$ oxyalkyl, or a branched or unbranched $C_{4-30}$ oxyalkenyl, each of which is optionally substituted by one or more substituents selected independently from $R^{13}$; $R^{12}$ is a branched or unbranched $C_{4-24}$ alkyl, a branched or unbranched $C_{4-24}$ alkenyl, a branched or unbranched $C_{4-30}$ oxyalkyl, or a branched or unbranched $C_{4-30}$ oxyalkenyl, each of which is optionally substituted by one or more substituents selected independently from $R^{13}$; and $R^{13}$ is a halogen atom, —OH, —NH$_2$, $C_{1-6}$ alkyl, $C_{1-6}$ heteroalkyl, $C_{2-6}$ alkenyl, or $C_{2-6}$ heteroalkenyl.

In some embodiments, $X^{11}$ is $C_{11-24}$ alkylene, optionally substituted one or more times with substituents selected independently from —OH and $C_{1-6}$ alkyloxy. In some embodiments, $X^{11}$ is $C_{12-24}$ alkylene, optionally substituted one or more times with substituents selected independently from —OH and $C_{1-6}$ alkyloxy. In some embodiments, $X^{11}$ is $C_{12-20}$ alkylene, optionally substituted one or more times with substituents selected independently from —OH and $C_{1-6}$ alkyloxy. In some embodiments, $X^{11}$ is $C_{14-20}$ alkylene, optionally substituted one or more times with substituents selected independently from —OH and $C_{1-6}$ alkyloxy. In some embodiments, $X^{11}$ is $C_{14-18}$ alkylene, optionally substituted one or more times with substituents selected independently from —OH and $C_{1-6}$ alkyloxy. In some embodiments, $X^{11}$ is $C_{16}$ alkylene, optionally substituted one or more times with substituents selected independently from —OH and $C_{1-6}$ alkyloxy. In some embodiments, $X^{11}$ is —(CH$_2$)$_{12}$—, —(CH$_2$)$_{14}$—, —(CH$_2$)$_{16}$—, —(CH$_2$)$_{18}$—, —(CH$_2$)$_{20}$—, or —(CH$_2$)$_{22}$—. In some such embodiments, $X^{11}$ is —(CH$_2$)$_{14}$—, —(CH$_2$)$_{16}$—, or —(CH$_2$)$_{20}$—. In some embodiments, $X^{11}$ is —(CH$_2$)$_{16}$—.

In some embodiments, $X^{11}$ is $C_{11-24}$ alkenylene, optionally substituted one or more times with substituents selected independently from —OH and $C_{1-6}$ alkyloxy. In some embodiments, $X^{11}$ is $C_{12-24}$ alkenylene, optionally substituted one or more times with substituents selected independently from —OH and $C_{1-6}$ alkyloxy. In some embodiments, $X^{11}$ is $C_{12-20}$ alkenylene, optionally substituted one or more times with substituents selected independently from —OH and $C_{1-6}$ alkyloxy. In some embodiments, $X^{11}$ is $C_{14-20}$ alkenylene, optionally substituted one or more times with substituents selected independently from —OH and $C_{1-6}$ alkyloxy. In some embodiments, $X^{11}$ is $C_{14-18}$ alkenylene, optionally substituted one or more times with substituents selected independently from —OH and $C_{1-6}$ alkyloxy. In some embodiments, $X^{11}$ is $C_{16}$ alkenylene, optionally substituted one or more times with substituents selected independently from —OH and $C_{1-6}$ alkyloxy. In some embodiments, $X^{11}$ is —(CH$_2$)$_7$—CH=CH=(CH$_2$)$_7$—. In some other embodiments, $X^{11}$ is —(CH$_2$)$_5$—CH=CH=(CH$_2$)$_5$—. In some other embodiments, $X^{11}$ is —(CH$_2$)$_9$—CH=CH=(CH$_2$)$_9$—.

In certain further embodiments of any of the above embodiments, $R^{11}$ is an unbranched $C_{4-24}$, which is optionally substituted by one or more substituents selected independently from $R^{13}$. In some further embodiments, $R^{11}$ is an unbranched $C_{4-20}$ alkyl, which is optionally substituted by one or more substituents selected independently from —OH and $C_{1-6}$ alkyloxy. In some embodiments, $R^{11}$ is butyl, pentyl, hexyl, heptyl, or octyl.

In some embodiments, $R^{11}$ is a branched $C_{4-24}$ alkyl, which is optionally substituted by one or more substituents selected independently from $R^{13}$. In some further embodiments, $R^{11}$ is a branched $C_{4-20}$ alkyl, which comprises branching at the 1-position of the alkyl moiety, and which is optionally substituted by one or more substituents selected independently from —OH and $C_{1-6}$ alkyloxy. In some embodiments, $R^{11}$ is a branched $C_{4-20}$ alkyl, which comprises branching at the 2-position of the alkyl moiety, and which is optionally substituted by one or more substituents selected independently from —OH and $C_{1-6}$ alkyloxy. In some embodiments, $R^{11}$ is a branched $C_{4-20}$ alkyl, which comprises branching at the 3-position of the alkyl moiety, and which is optionally substituted by one or more substituents selected independently from —OH and $C_{1-6}$ alkyloxy. In some embodiments, $R^{11}$ is a branched $C_{4-20}$ alkyl, which has no branching at the 1-position of the alkyl moiety, and which is optionally substituted by one or more substituents selected independently from —OH and $C_{1-6}$ alkyloxy. In some embodiments, $R^{11}$ is 2-methylpentyl, 2-ethylhexyl, 2-butyloctyl, and 3-methylbutyl.

In some embodiments, $R^{11}$ is $C_{4-30}$ oxyalkyl, which is optionally substituted by one or more substituents selected independently from —OH and $C_{1-6}$ alkyloxy. In some embodiments, $R^{11}$ is $C_{4-24}$ oxyalkyl, which is optionally substituted by one or more substituents selected independently from —OH and $C_{1-6}$ alkyloxy. In some embodiments, $R^{11}$ is —(CH$_2$—CH$_2$—O)$_{1-14}$—R$^y$ or —(CH$_2$—CH$_2$—O)$_{1-12}$—R$^y$, where R$^y$ is $C_{1-6}$ unbranched alkyl. In some embodiments, R$^y$ is methyl. In some other embodiments, R$^y$ is ethyl. In some embodiments, $R^{11}$ is —CH$_2$—CH$_2$—O—CH$_3$. In some embodiments, $R^{11}$ is —(CH$_2$—CH$_2$—O)$_2$—CH$_3$. In some embodiments, $R^{11}$ is —(CH$_2$—CH$_2$—O)$_3$—CH$_3$. In some embodiments, $R^{11}$ is —(CH$_2$—CH$_2$—O)$_4$—CH$_3$. In some embodiments, $R^{11}$ is —(CH$_2$—CH$_2$—O)$_5$—CH$_3$. In some embodiments, $R^{11}$ is —(CH$_2$—CH$_2$—O)$_6$—CH$_3$. In some embodiments, $R^{11}$ is —(CH$_2$—CH$_2$—O)$_7$—CH$_3$. In some embodiments, $R^{11}$ is —(CH$_2$—CH$_2$—O)$_8$—CH$_3$. In some embodiments, $R^{11}$ is —(CH$_2$—CH$_2$—O)$_9$—CH$_3$. In some embodiments, $R^{11}$ is —(CH$_2$—CH$_2$—O)$_{10}$—CH$_3$. In some embodiments, $R^{11}$ is —(CH$_2$—CH$_2$—O)$_{11}$—CH$_3$. In some embodiments, $R^{11}$ is —(CH$_2$—CH$_2$—O)$_{12}$—CH$_3$.

In certain further embodiments of any of the above embodiments, $R^{12}$ is an unbranched $C_{4-24}$, which is optionally substituted by one or more substituents selected independently from $R^{13}$. In some further embodiments, $R^{12}$ is an unbranched $C_{4-20}$ alkyl, which is optionally substituted by one or more substituents selected independently from —OH and $C_{1-6}$ alkyloxy. In some embodiments, $R^{12}$ is butyl, pentyl, hexyl, heptyl, or octyl.

In some embodiments, $R^{12}$ is a branched $C_{4-24}$ alkyl, which is optionally substituted by one or more substituents selected independently from $R^{13}$. In some further embodiments, $R^{12}$ is a branched $C_{4-20}$ alkyl, which comprises branching at the 1-position of the alkyl moiety, and which is optionally substituted by one or more substituents selected independently from —OH and $C_{1-6}$ alkyloxy. In some embodiments, $R^{12}$ is a branched $C_{4-20}$ alkyl, which comprises branching at the 2-position of the alkyl moiety, and which is optionally substituted by one or more substituents selected independently from —OH and $C_{1-6}$ alkyloxy. In some embodiments, $R^{12}$ is a branched $C_{4-20}$ alkyl, which comprises branching at the 3-position of the alkyl moiety, and which is optionally substituted by one or more substituents selected independently from —OH and $C_{1-6}$ alkyloxy. In some embodiments, $R^{12}$ is a branched $C_{4-20}$ alkyl, which has no branching at the 1-position of the alkyl moiety, and which is optionally substituted by one or more substituents selected independently from —OH and $C_{1-6}$ alkyloxy. In some embodiments, $R^{12}$ is 2-methylpentyl, 2-ethylhexyl, 2-butyloctyl, and 3-methylbutyl.

In some embodiments, $R^{12}$ is $C_{4-30}$ oxyalkyl, which is optionally substituted by one or more substituents selected independently from —OH and $C_{1-6}$ alkyloxy. In some embodiments, $R^{12}$ is $C_{4-24}$ oxyalkyl, which is optionally substituted by one or more substituents selected independently from —OH and $C_{1-6}$ alkyloxy. In some embodiments, $R^{12}$ is —(CH$_2$—CH$_2$—O)$_{1-14}$—R$^{y'}$ or —(CH$_2$—CH$_2$—O)$_{1-12}$—R$^{y'}$, where R$^{y'}$ is $C_{1-6}$ unbranched alkyl. In some embodiments, $R^{y''}$ is methyl. In some embodiments, $R^{y''}$ is ethyl. In some embodiments, $R^{12}$ is —$CH_2$—$CH_2$—O—$CH_3$. In some embodiments, $R^{12}$ is —$(CH_2$—$CH_2$—$O)_2$—$CH_3$. In some embodiments, $R^{12}$ is —$(CH_2$—$CH_2$—$O)_3$—$CH_3$. In some embodiments, $R^{12}$ is —$(CH_2$—$CH_2$—$O)_4$—$CH_3$. In some embodiments, $R^{12}$ is —$(CH_2$—$CH_2$—$O)_5$—$CH_3$. In some embodiments, $R^{12}$ is —$(CH_2$—$CH_2$—$O)_6$—$CH_3$. In some embodiments, $R^{12}$ is —$(CH_2$—$CH_2$—$O)_7$—$CH_3$. In some embodiments, $R^{12}$ is —$(CH_2$—$CH_2$—$O)_8$—$CH_3$. In some embodiments, $R^{12}$ is —$(CH_2$—$CH_2$—$O)_9$—$CH_3$. In some embodiments, $R^{12}$ is —$(CH_2$—$CH_2$—$O)_{10}$—$CH_3$. In some embodiments, $R^{12}$ is —$(CH_2$—$CH_2$—$O)_{11}$—$CH_3$. In some embodiments, $R^{12}$ is —$(CH_2$—$CH_2$—$O)_{12}$—$CH_3$.

In some embodiments of any of the above embodiments, $R^{11}$ and $R^{12}$ are the same. In some other embodiments, $R^{11}$ and $R^{12}$ are not the same.

In some embodiments, the plasticizer composition consists of one or diesters according to any of the above embodiments. In some embodiments, the plasticizer composition consists essentially of one or diesters according to any of the above embodiments.

In some embodiments, the plasticizer composition includes one or more additional components, i.e., in addition to one of more of the diesters of any of the preceding embodiments. For example, in some embodiments, the plasticizer composition includes one or more additional plasticizers. Any suitable plasticizers can be used. For example, in some embodiments, the one or more additional plasticizers are plasticizers that are compatible for use with polymeric resins, including, but not limited to, phthalates, adipates, trimellitic esters, phosphate esters, sebacates, azelates, sulphonates, epoxidized fatty acid esters, or any combination thereof. Such compounds include, but are not limited to, benzenedicarboxylic esters, citraconic esters, 2-hydroxy-1,2,3-propanetricarboxylic esters, malonic esters, succinates, vegetable and animal oils, benzoic esters, triethylene glycol dihexanoate, tetraethylene glycol diheptanoate, linear alkylbenzenes (LABs), branched alkylbenzenes (BABs), polyethylene glycols, polyethylene glycol ethers, polypropylene glycols, polypropylene glycol ethers, or any combinations thereof.

In some embodiments, the plasticizer can include one or more additional additives. Any suitable additives can be used, so long as they are generally compatible with the plasticizing components of the composition. In some embodiments, the plasticizer composition includes metal oxides, such as silica, alumina, titania, and the like; antioxidants; colorants; color modifiers; diluents; or any combinations thereof.

Polymer Compositions

In certain aspects, the disclosure provides polymer compositions that include a polymeric resin and a plasticizer composition of any of the embodiments disclosed above. Any suitable polymeric resin can be used. For example, in some embodiments, the polymeric resin is: a vinyl chloride resin, such as polyvinyl chloride (PVC); polyvinyl butyral (PVB); a polysulfide; a polyurethane; an acrylic resin; an epichlorohydrins; nitrile rubber; chloro sulfonated polyethylene; chlorinated polyethylene; polychloroprene; styrene butadiene rubber; natural rubber; synthetic rubber; EPDM rubber; propylene-based polymers, such as polypropylene; ethylene-based polymers, such as polyethylene; or any combinations, blends, or copolymers thereof. In some embodiments, the polymeric resin is polyvinyl chloride (PVC) or any blends or copolymers thereof. In some other embodiments, the polymeric resin is polyvinyl butyral (PVB) or any blends of copolymers thereof.

In some embodiments, the polymer composition can include one or more additives in addition to the polymeric resin and the plasticizer composition. Any suitable additives can be used. For example, in some embodiments, the polymer composition can include a filler (e.g., calcium carbonate, clays, and metal oxides, such as silica, alumina, or titania), a flame retardant, a heat stabilizer, an anti-drip agent, a colorant, a lubricant, a low molecular weight polyethylene, a hindered amine light stabilizer, a UV light absorber, a curing agent, a booster, a retardant, a processing aid, a coupling agent, an antistatic agent, a nucleating agent, a slip agent, a viscosity control agent, a tackifier, an anti-blocking agent, a surfactant, an extender oil, an acid scavenger, a metal deactivator, metal soap stabilizers (e.g., zinc stearate or mixed metal stabilizers containing Ca, Zn, Mg, Sn, and any combination thereof), an antioxidant (e.g., a phenolic antioxidant), a processing aid, or any combinations thereof.

Methods of Making Diesters

The diesters disclosed above can be made by conventional means. For example, in some embodiments, the diesters are made by reacting a dibasic acid with an alcohol or a mixture of alcohols to provide the dibasic ester by condensation. In some instances, diesters can also be made by transesterification, where a dibasic ester, such as a dimethyl dibasic ester is reacted with a longer-chain alcohol or mixture of longer-chain alcohols to provide the dibasic ester.

Derivation from Renewable Sources

The compounds employed in any of the aspects or embodiments disclosed herein can, in certain embodiments, be derived from renewable sources, such as from various natural oils or their derivatives. Any suitable methods can be used to make these compounds from such renewable sources. Suitable methods include, but are not limited to, fermentation, conversion by bioorganisms, and conversion by metathesis.

Olefin metathesis provides one possible means to convert certain natural oil feedstocks into olefins and esters that can be used in a variety of applications, or that can be further modified chemically and used in a variety of applications. In some embodiments, a composition (or components of a composition) may be formed from a renewable feedstock, such as a renewable feedstock formed through metathesis reactions of natural oils and/or their fatty acid or fatty ester derivatives. When compounds containing a carbon-carbon double bond undergo metathesis reactions in the presence of a metathesis catalyst, some or all of the original carbon-carbon double bonds are broken, and new carbon-carbon double bonds are formed. The products of such metathesis reactions include carbon-carbon double bonds in different locations, which can provide unsaturated organic compounds having useful chemical properties.

A wide range of natural oils, or derivatives thereof, can be used in such metathesis reactions. Examples of suitable natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

The natural oil may include canola or soybean oil, such as refined, bleached and deodorized soybean oil (i.e., RBD soybean oil). Soybean oil typically includes about 95 percent by weight (wt %) or greater (e.g., 99 wt % or greater) triglycerides of fatty acids. Major fatty acids in the polyol esters of soybean oil include but are not limited to saturated fatty acids such as palmitic acid (hexadecanoic acid) and stearic acid (octadecanoic acid), and unsaturated fatty acids such as oleic acid (9-octadecenoic acid), linoleic acid (9,12-octadecadienoic acid), and linolenic acid (9,12,15-octadecatrienoic acid).

Metathesized natural oils can also be used. Examples of metathesized natural oils include but are not limited to a metathesized vegetable oil, a metathesized algal oil, a metathesized animal fat, a metathesized tall oil, a metathesized derivatives of these oils, or mixtures thereof. For example, a metathesized vegetable oil may include metathesized canola oil, metathesized rapeseed oil, metathesized coconut oil, metathesized corn oil, metathesized cottonseed oil, metathesized olive oil, metathesized palm oil, metathesized peanut oil, metathesized safflower oil, metathesized sesame oil, metathesized soybean oil, metathesized sunflower oil, metathesized linseed oil, metathesized palm kernel oil, metathesized tung oil, metathesized jatropha oil, metathesized mustard oil, metathesized camelina oil, metathesized pennycress oil, metathesized castor oil, metathesized derivatives of these oils, or mixtures thereof. In another example, the metathesized natural oil may include a metathesized animal fat, such as metathesized lard, metathesized tallow, metathesized poultry fat, metathesized fish oil, metathesized derivatives of these oils, or mixtures thereof.

Such natural oils, or derivatives thereof, can contain esters, such as triglycerides, of various unsaturated fatty acids. The identity and concentration of such fatty acids varies depending on the oil source, and, in some cases, on the variety. In some embodiments, the natural oil comprises one or more esters of oleic acid, linoleic acid, linolenic acid, or any combination thereof. When such fatty acid esters are metathesized, new compounds are formed. For example, in embodiments where the metathesis uses certain short-chain olefins, e.g., ethylene, propylene, or 1-butene, and where the natural oil includes esters of oleic acid, an amount of 1-decene and 1-decenoid acid (or an ester thereof), among other products, are formed. Following transesterification, for example, with an alkyl alcohol, an amount of 9-denenoic acid alkyl ester is formed. In some such embodiments, a separation step may occur between the metathesis and the transesterification, where the alkenes are separated from the esters. In some other embodiments, transesterification can occur before metathesis, and the metathesis is performed on the transesterified product.

In some embodiments, the natural oil can be subjected to various pre-treatment processes, which can facilitate their utility for use in certain metathesis reactions. Useful pre-treatment methods are described in United States Patent Application Publication Nos. 2011/0113679, 2014/0275595, and 2014/0275681, all three of which are hereby incorporated by reference as though fully set forth herein.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself. In other embodiments, the natural oil or unsaturated ester undergoes a cross-metathesis reaction with the low-molecular-weight olefin or mid-weight olefin. The self-metathesis and/or cross-metathesis reactions form a metathesized product wherein the metathesized product comprises olefins and esters.

In some embodiments, the low-molecular-weight olefin (or short-chain olefin) is in the $C_{2-6}$ range. As a non-limiting example, in one embodiment, the low-molecular-weight olefin may comprise at least one of: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some embodiments, the short-chain olefin is 1-butene. In some instances, a higher-molecular-weight olefin can also be used.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride (as described above). In some such embodiments, the metathesis is a cross-metathesis of any of the aforementioned unsaturated triglyceride species with another olefin, e.g., an alkene. In some such embodiments, the alkene used in the cross-metathesis is a lower alkene, such as ethylene, propylene, 1-butene, 2-butene, etc. In some embodiments, the alkene is ethylene. In some other embodiments, the alkene is propylene. In some further embodiments, the alkene is 1-butene. And in some even further embodiments, the alkene is 2-butene.

Metathesis reactions can provide a variety of useful products, when employed in the methods disclosed herein. For example, the unsaturated esters may be derived from a natural oil feedstock, in addition to other valuable compositions. Moreover, in some embodiments, a number of valuable compositions can be targeted through the self-metathesis reaction of a natural oil feedstock, or the cross-metathesis reaction of the natural oil feedstock with a low-molecular-weight olefin or mid-weight olefin, in the presence of a metathesis catalyst. Such valuable compositions can include fuel compositions, detergents, surfactants, and other specialty chemicals. Additionally, transesterified products (i.e., the products formed from transesterifying an ester in the presence of an alcohol) may also be targeted, non-limiting examples of which include: fatty acid methyl esters ("FAMEs"); biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA; dimers of the transesterified products; and mixtures thereof.

Further, in some embodiments, multiple metathesis reactions can also be employed. In some embodiments, the multiple metathesis reactions occur sequentially in the same reactor. For example, a glyceride containing linoleic acid can be metathesized with a terminal lower alkene (e.g., ethylene, propylene, 1-butene, and the like) to form 1,4-decadiene, which can be metathesized a second time with a terminal lower alkene to form 1,4-pentadiene. In other embodiments, however, the multiple metathesis reactions are not sequential, such that at least one other step (e.g., transesterification, hydrogenation, etc.) can be performed between the first metathesis step and the following metathesis step. These multiple metathesis procedures can be used to obtain products that may not be readily obtainable from a single metathesis reaction using available starting materials. For example, in some embodiments, multiple metathesis can involve self-metathesis followed by cross-metathesis to obtain metathesis dimers, trimmers, and the like. In some other embodiments, multiple metathesis can be used to obtain olefin and/or ester components that have chain lengths that may not be achievable from a single metathesis reaction with a natural oil triglyceride and typical lower alkenes (e.g., ethylene, propylene, 1-butene, 2-butene, and the like). Such multiple metathesis can be useful in an industrial-scale reactor, where it may be easier to perform multiple metathesis than to modify the reactor to use a different alkene.

For example, multiple metathesis can be employed to make the dibasic acid compounds used to make the diesters disclosed herein. In some embodiments, alkyl (e.g., methyl) esters of 9-decenoic acid, 9-undecenoic acid, 9-dodecenoic acid, or any combination thereof, can be reacted in a self-metathesis reaction or a cross-metathesis to generate various unsaturated dibasic alkyl esters, such as dimethyl 9-octadecendioate. Such compounds can then be converted to dibasic acids by hydrolysis or via saponification followed by acidification. If a saturated dibasic acid is desired, the compound can be hydrogenated, either before conversion to the acid or after. Dibasic acids of other chain lengths can be made by analogous means.

The conditions for such metathesis reactions, and the reactor design, and suitable catalysts are as described below with reference to the metathesis of the olefin esters. That discussion is incorporated by reference as though fully set forth herein.

Olefin Metathesis

In some embodiments, one or more of the unsaturated monomers can be made by metathesizing a natural oil or natural oil derivative. The terms "metathesis" or "metathesizing" can refer to a variety of different reactions, including, but not limited to, cross-metathesis, self-metathesis, ring-opening metathesis, ring-opening metathesis polymerizations ("ROMP"), ring-closing metathesis ("RCM"), and acyclic diene metathesis ("ADMET"). Any suitable metathesis reaction can be used, depending on the desired product or product mixture.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself. In other embodiments, the natural oil or unsaturated ester undergoes a cross-metathesis reaction with the low-molecular-weight olefin or mid-weight olefin. The self-metathesis and/or cross-metathesis reactions form a metathesized product wherein the metathesized product comprises olefins and esters.

In some embodiments, the low-molecular-weight olefin is in the $C_{2-6}$ range. As a non-limiting example, in one embodiment, the low-molecular-weight olefin may comprise at least one of: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some instances, a higher-molecular-weight olefin can also be used.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride (as described above). In some such embodiments, the metathesis is a cross-metathesis of any of the aforementioned unsaturated triglyceride species with another olefin, e.g., an alkene. In some such embodiments, the alkene used in the cross-metathesis is a lower alkene, such as ethylene, propylene, 1-butene, 2-butene, etc. In some embodiments, the alkene is ethylene. In some other embodiments, the alkene is propylene. In some further embodiments, the alkene is 1-butene. And in some even further embodiments, the alkene is 2-butene.

Metathesis reactions can provide a variety of useful products, when employed in the methods disclosed herein. For example, terminal olefins and internal olefins may be derived from a natural oil feedstock, in addition to other valuable compositions. Moreover, in some embodiments, a number of valuable compositions can be targeted through the self-metathesis reaction of a natural oil feedstock, or the cross-metathesis reaction of the natural oil feedstock with a low-molecular-weight olefin or mid-weight olefin, in the presence of a metathesis catalyst. Such valuable compositions can include fuel compositions, detergents, surfactants, and other specialty chemicals. Additionally, transesterified products (i.e., the products formed from transesterifying an ester in the presence of an alcohol) may also be targeted, non-limiting examples of which include: fatty acid methyl esters ("FAMEs"); biodiesel; 9-decenoic acid ("9DA") esters, 9-undecenoic acid ("9UDA") esters, and/or 9-dodecenoic acid ("9DDA") esters; 9DA, 9UDA, and/or 9DDA;

alkali metal salts and alkaline earth metal salts of 9DA, 9UDA, and/or 9DDA; dimers of the transesterified products; and mixtures thereof.

Further, in some embodiments, the methods disclosed herein can employ multiple metathesis reactions. In some embodiments, the multiple metathesis reactions occur sequentially in the same reactor. For example, a glyceride containing linoleic acid can be metathesized with a terminal lower alkene (e.g., ethylene, propylene, 1-butene, and the like) to form 1,4-decadiene, which can be metathesized a second time with a terminal lower alkene to form 1,4-pentadiene. In other embodiments, however, the multiple metathesis reactions are not sequential, such that at least one other step (e.g., transesterification, hydrogenation, etc.) can be performed between the first metathesis step and the following metathesis step. These multiple metathesis procedures can be used to obtain products that may not be readily obtainable from a single metathesis reaction using available starting materials. For example, in some embodiments, multiple metathesis can involve self-metathesis followed by cross-metathesis to obtain metathesis dimers, trimmers, and the like. In some other embodiments, multiple metathesis can be used to obtain olefin and/or ester components that have chain lengths that may not be achievable from a single metathesis reaction with a natural oil triglyceride and typical lower alkenes (e.g., ethylene, propylene, 1-butene, 2-butene, and the like). Such multiple metathesis can be useful in an industrial-scale reactor, where it may be easier to perform multiple metathesis than to modify the reactor to use a different alkene.

The metathesis process can be conducted under any conditions adequate to produce the desired metathesis products. For example, stoichiometry, atmosphere, solvent, temperature, and pressure can be selected by one skilled in the art to produce a desired product and to minimize undesirable byproducts. In some embodiments, the metathesis process may be conducted under an inert atmosphere. Similarly, in embodiments where a reagent is supplied as a gas, an inert gaseous diluent can be used in the gas stream. In such embodiments, the inert atmosphere or inert gaseous diluent typically is an inert gas, meaning that the gas does not interact with the metathesis catalyst to impede catalysis to a substantial degree. For example, non-limiting examples of inert gases include helium, neon, argon, and nitrogen, used individually or in with each other and other inert gases.

The rector design for the metathesis reaction can vary depending on a variety of factors, including, but not limited to, the scale of the reaction, the reaction conditions (heat, pressure, etc.), the identity of the catalyst, the identity of the materials being reacted in the reactor, and the nature of the feedstock being employed. Suitable reactors can be designed by those of skill in the art, depending on the relevant factors, and incorporated into a refining process such, such as those disclosed herein.

The metathesis reactions disclosed herein generally occur in the presence of one or more metathesis catalysts. Such methods can employ any suitable metathesis catalyst. The metathesis catalyst in this reaction may include any catalyst or catalyst system that catalyzes a metathesis reaction. Any known metathesis catalyst may be used, alone or in combination with one or more additional catalysts. Examples of metathesis catalysts and process conditions are described in US 2011/0160472, incorporated by reference herein in its entirety, except that in the event of any inconsistent disclosure or definition from the present specification, the disclosure or definition herein shall be deemed to prevail. A number of the metathesis catalysts described in US 2011/0160472 are presently available from Materia, Inc. (Pasadena, Calif.).

In some embodiments, the metathesis catalyst includes a Grubbs-type olefin metathesis catalyst and/or an entity derived therefrom. In some embodiments, the metathesis catalyst includes a first-generation Grubbs-type olefin metathesis catalyst and/or an entity derived therefrom. In some embodiments, the metathesis catalyst includes a second-generation Grubbs-type olefin metathesis catalyst and/or an entity derived therefrom. In some embodiments, the metathesis catalyst includes a first-generation Hoveyda-Grubbs-type olefin metathesis catalyst and/or an entity derived therefrom. In some embodiments, the metathesis catalyst includes a second-generation Hoveyda-Grubbs-type olefin metathesis catalyst and/or an entity derived therefrom. In some embodiments, the metathesis catalyst includes one or a plurality of the ruthenium carbene metathesis catalysts sold by Materia, Inc. of Pasadena, Calif. and/or one or more entities derived from such catalysts. Representative metathesis catalysts from Materia, Inc. for use in accordance with the present teachings include but are not limited to those sold under the following product numbers as well as combinations thereof: product no. C823 (CAS no. 172222-30-9), product no. C848 (CAS no. 246047-72-3), product no. C601 (CAS no. 203714-71-0), product no. C627 (CAS no. 301224-40-8), product no. C571 (CAS no. 927429-61-6), product no. C598 (CAS no. 802912-44-3), product no. C793 (CAS no. 927429-60-5), product no. C801 (CAS no. 194659-03-9), product no. C827 (CAS no. 253688-91-4), product no. C884 (CAS no. 900169-53-1), product no. C833 (CAS no. 1020085-61-3), product no. C859 (CAS no. 832146-68-6), product no. C711 (CAS no. 635679-24-2), product no. C933 (CAS no. 373640-75-6).

In some embodiments, the metathesis catalyst includes a molybdenum and/or tungsten carbene complex and/or an entity derived from such a complex. In some embodiments, the metathesis catalyst includes a Schrock-type olefin metathesis catalyst and/or an entity derived therefrom. In some embodiments, the metathesis catalyst includes a high-oxidation-state alkylidene complex of molybdenum and/or an entity derived therefrom. In some embodiments, the metathesis catalyst includes a high-oxidation-state alkylidene complex of tungsten and/or an entity derived therefrom. In some embodiments, the metathesis catalyst includes molybdenum (VI). In some embodiments, the metathesis catalyst includes tungsten (VI). In some embodiments, the metathesis catalyst includes a molybdenum- and/or a tungsten-containing alkylidene complex of a type described in one or more of (a) Angew. Chem. Int. Ed. Engl., 2003, 42, 4592-4633; (b) Chem. Rev., 2002, 102, 145-179; and/or (c) Chem. Rev., 2009, 109, 3211-3226, each of which is incorporated by reference herein in its entirety, except that in the event of any inconsistent disclosure or definition from the present specification, the disclosure or definition herein shall be deemed to prevail.

In certain embodiments, the metathesis catalyst is dissolved in a solvent prior to conducting the metathesis reaction. In certain such embodiments, the solvent chosen may be selected to be substantially inert with respect to the metathesis catalyst. For example, substantially inert solvents include, without limitation: aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In some embodiments, the solvent comprises toluene.

In other embodiments, the metathesis catalyst is not dissolved in a solvent prior to conducting the metathesis reaction. The catalyst, instead, for example, can be slurried with the natural oil or unsaturated ester, where the natural oil or unsaturated ester is in a liquid state. Under these conditions, it is possible to eliminate the solvent (e.g., toluene) from the process and eliminate downstream olefin losses when separating the solvent. In other embodiments, the metathesis catalyst may be added in solid state form (and not slurried) to the natural oil or unsaturated ester (e.g., as an auger feed).

The metathesis reaction temperature may, in some instances, be a rate-controlling variable where the temperature is selected to provide a desired product at an acceptable rate. In certain embodiments, the metathesis reaction temperature is greater than −40° C., or greater than −20° C., or greater than 0° C., or greater than 10° C. In certain embodiments, the metathesis reaction temperature is less than 200° C., or less than 150° C., or less than 120° C. In some embodiments, the metathesis reaction temperature is between 0° C. and 150° C., or is between 10° C. and 120° C.

The metathesis reaction can be run under any desired pressure. In some instances, it may be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than 0.1 atm (10 kPa), or greater than 0.3 atm (30 kPa), or greater than 1 atm (100 kPa). In some embodiments, the reaction pressure is no more than about 70 atm (7000 kPa), or no more than about 30 atm (3000 kPa). In some embodiments, the pressure for the metathesis reaction ranges from about 1 atm (100 kPa) to about 30 atm (3000 kPa).

Methods of Increasing the Plasticity of a Resin

In certain aspects, the disclosure provides methods of increasing the plasticity of a polymeric resin, comprising: providing a polymeric resin; and contacting the polymeric resin with the plasticizer composition of any one of the above embodiments.

In some embodiments, the contacting of the polymeric resin with the plasticizer composition comprises contacting the polymeric resin with a plasticizing effective amount of the plasticizer composition. A plasticizing effective amount will vary depending on a number of factors, including, but not limited to, the chemical structure of the resin, the desired amount of plasticity, the chemical makeup of the plasticizing composition, and the like.

Any suitable resin can be plasticized. In some embodiments, the polymeric resin is: a vinyl chloride resin, such as polyvinyl chloride (PVC); polyvinyl butyral (PVB); a polysulfide; a polyurethane; an acrylic resin; an epichlorohydrins; nitrile rubber; chloro sulfonated polyethylene; chlorinated polyethylene; polychloroprene; styrene butadiene rubber; natural rubber; synthetic rubber; EPDM rubber; propylene-based polymers, such as polypropylene; ethylene-based polymers, such as polyethylene; or any combinations, blends, or copolymers thereof. In some embodiments, the polymeric resin is polyvinyl chloride (PVC). In some embodiments, the polymeric resin is polyvinyl butyral (PVB).

Methods of Lowering the Glass Transition Temperature of a Resin

In certain aspects, the disclosure provides methods of lowering the glass transition temperature ($T_g$) of a polymeric resin, comprising: providing a polymeric resin; and contacting the polymeric resin with the plasticizer composition of any one of the above embodiments.

Any suitable amount of the plasticizer composition can be used. The amount will vary depending on a number of factors, including, but not limited to, the chemical structure of the resin, the desired degree of lowering, the chemical makeup of the plasticizing composition, and the like.

Any suitable resin can be subjected to such treatment. In some embodiments, the polymeric resin is: a vinyl chloride resin, such as polyvinyl chloride (PVC); polyvinyl butyral (PVB); a polysulfide; a polyurethane; an acrylic resin; an epichlorohydrins; nitrile rubber; chloro sulfonated polyethylene; chlorinated polyethylene; polychloroprene; styrene butadiene rubber; natural rubber; synthetic rubber; EPDM rubber; propylene-based polymers, such as polypropylene; ethylene-based polymers, such as polyethylene; or any combinations, blends, or copolymers thereof. In some embodiments, the polymeric resin is polyvinyl chloride (PVC). In some embodiments, the polymeric resin is polyvinyl butyral (PVB).

Laminated Articles

In a certain aspects and embodiments, the disclosure provides a laminated article, comprising: a first transparent layer; and a second transparent layer disposed on the first transparent layer, the second transparent layer comprising a polymer composition.

Any suitable transparent material can be used as the first transparent layer. Examples include, but are not limited to, polycarbonate and various kinds of glass. In some embodiments, the first transparent layer is a glass sheet.

The polymer composition can include any of suitable polymer composition. Suitable polymer compositions include those disclosed above, such as those described above that include a polymer and one or more compounds of formula (II). In some embodiments, the second transparent layer is disposed directly on the first transparent layer, such that there is no intervening layer. In some other embodiments, however, there can be one or more intervening layers that separate the first transparent layer from the second transparent layer, such that the second transparent layer is indirectly disposed on the first transparent layer.

In some further embodiments, the laminated article includes a third transparent layer disposed on the second transparent layer opposite the first transparent layer. Any suitable transparent material can be used as the third transparent layer. Examples include, but are not limited to, polycarbonate and various kinds of glass. In some embodiments, the third transparent layer is a glass sheet. Further, in some embodiments, the third transparent layer is disposed directly on the second transparent layer, such that there is no intervening layer. In some other embodiments, however, there can be one or more intervening layers that separate the third transparent layer from the second transparent layer, such that the second transparent layer is indirectly disposed on the third transparent layer.

Photovoltaic Articles

In a certain aspects and embodiments, the disclosure provides a laminated article, comprising: a first transparent layer having a photovoltaic cell (or a portion of a photovoltaic cell) disposed thereon; and a second transparent layer disposed on the first transparent layer, the second transparent layer comprising a polymer composition.

Any suitable transparent material can be used as the first transparent layer. Examples include, but are not limited to, polycarbonate and various kinds of glass. In some embodiments, the first transparent layer is a glass sheet.

The polymer composition can include any of suitable polymer composition. Suitable polymer compositions include those disclosed above, such as those described above that include a polymer and one or more compounds of formula (II). In some embodiments, the second transparent layer is disposed directly on the first transparent layer, such that there is no intervening layer. In some other embodiments, however, there can be one or more intervening layers that separate the first transparent layer from the second transparent layer, such that the second transparent layer is indirectly disposed on the first transparent layer.

The photovoltaic cell can be any suitable photovoltaic cell, such as those commonly known in the art. In some embodiments, the photovoltaic cell is made of a transparent material. Suitable examples of such transparent materials include, but are not limited to, transparent conductive polymers, indium tin oxide (ITO), and the like.

In some further embodiments, the laminated article includes a third transparent layer disposed on the second transparent layer opposite the first transparent layer. Any suitable transparent material can be used as the third transparent layer. Examples include, but are not limited to, polycarbonate and various kinds of glass. In some embodiments, the third transparent layer is a glass sheet. Further, in some embodiments, the third transparent layer is disposed directly on the second transparent layer, such that there is no intervening layer. In some other embodiments, however, there can be one or more intervening layers that separate the third transparent layer from the second transparent layer, such that the second transparent layer is indirectly disposed on the third transparent layer.

Electrochromic Articles

In a eighth aspect, the disclosure provides a laminated article, comprising: a first transparent layer; and a second transparent layer disposed on the first transparent layer, the second transparent layer comprising a polymer composition of the third aspect and one or more electrochromic materials.

Any suitable transparent material can be used as the first transparent layer. Examples include, but are not limited to, polycarbonate and various kinds of glass. In some embodiments, the first transparent layer is a glass sheet.

The polymer composition can include any of suitable polymer composition. Suitable polymer compositions include those disclosed above, such as those described above that include a polymer and one or more compounds of formula (II). In some embodiments, the second transparent layer is disposed directly on the first transparent layer, such that there is no intervening layer. In some other embodiments, however, there can be one or more intervening layers that separate the first transparent layer from the second transparent layer, such that the second transparent layer is indirectly disposed on the first transparent layer.

The electrochromic material can be any suitable electrochromic material, such as those commonly known in the art. In some embodiments, the electrochromic material is made of a transparent material.

In some further embodiments, the laminated article includes a third transparent layer disposed on the second transparent layer opposite the first transparent layer. Any suitable transparent material can be used as the third transparent layer. Examples include, but are not limited to, polycarbonate and various kinds of glass. In some embodiments, the third transparent layer is a glass sheet. Further, in some embodiments, the third transparent layer is disposed directly on the second transparent layer, such that there is no intervening layer. In some other embodiments, however, there can be one or more intervening layers that separate the third transparent layer from the second transparent layer, such that the second transparent layer is indirectly disposed on the third transparent layer.

EXAMPLES

Example 1

Bis(2-buytloctyl)Octadecanedioate

Octadecanedioic acid (ODDA, 5.00 g) was added to a 100-mL three-necked round-bottom flask. A Dean-Stark condenser was attached, followed by the addition of toluene to the ODDA and to the trap. 2-Butyloctyl alcohol (11 mL) was added to the ODDA mixture. The flask was immediately purged with nitrogen gas and p-toluenesulfonic acid (0.17 g) was added. The reaction mixture was heated to 115° C. and the reaction proceeded for 5 hours. Heat was then removed and the reaction mixture was allowed to cool to 60° C., at which point aqueous $NaHCO_3$ (saturated) was added to achieve a neutral pH. After vigorous stirring, the organic layer was separated and dried over $Na_2SO_4$. The dried product was then subjected to a vacuum treatment to remove any residual solvent. A yellow oil was obtained. Analysis by $^1H$ NMR provided the following chemical shifts: (400 MHz, $CDCl_3$) δ 0.85-1.10 (m, 88H), 1.20-1.38 (m, 346H), 1.40-1.50 (m, 10H), 1.55 (s, 12H), 1.65 (t, 33H), 2.30 (t, 20H), 3.97 (d, 21H). Analysis by $^{13}C$ NMR provided the following chemical shifts: (400 MHz, $CDCl_3$) δ C, 174.169; CH, 67.037; $CH_2$, 22.672, 23.003, 25.093, 26.685, 28.931, 29.205, 29.326, 29.518, 29.646, 29.682, 29.702, 30.972, 31.297, 31.834, 34.500, 37.286; $CH_3$, 14.067, 14.115.

Polyvinyl butyral (PVB) films were prepared using varying amounts of bis(2-buytloctyl)octadecanedioate ranging from none to 40 percent by weight of the plasticizer, relative to the total weight of the polymer composition. Table 1 shows the glass transition temperature ($T_g$) for films of varying amount of plasticizer incorporation.

TABLE 1

| Plasticizer Loading (wt %) | $T_g$ (° C.) |
| --- | --- |
| 0 | 76.5 |
| 10 | 64.5 |
| 20 | 63.0 |
| 30 | 57.5 |
| 40 | 56.0 |

Example 2

Bis(2-methylpentyl)Octadecanedioate

Octadecanedioic acid (ODDA, 5.00 g) was added to a 100-mL three-necked round-bottom flask. A Dean-Stark condenser was attached, followed by the addition of toluene to the ODDA and to the trap. 2-Methylpentyl alcohol (5.90 mL) was added to the ODDA mixture. The flask was immediately purged with nitrogen gas and p-toluenesulfonic acid (0.17 g) was added. The reaction mixture was heated to 115° C. and the reaction proceeded for 5 hours. Heat was then removed and the reaction mixture was allowed to cool to 60° C., at which point aqueous $NaHCO_3$ (saturated) was added to achieve a neutral pH. After vigorous stirring, the organic layer was separated and dried over $Na_2SO_4$. The dried product was then subjected to a vacuum treatment to remove any residual solvent. A yellow oil was obtained. Analysis by $^1$H NMR provided the following chemical shifts: (400 MHz, CDCl$_3$) δ 0.90-0.85 (m), 1.10-1.20 (m), 1.21-1.50 (m), 1.55-1.7 (t), 1.77 (o), 2.30 (t), 3.85 (dd), 3.95 (dd). Analysis by $^{13}$C NMR provided the following chemical shifts: (400 MHz, CDCl$_3$) δ C, 173.947; CH, 32.366; CH$_2$, 69.200, 35.691, 34.438, 29.701, 29.684, 29.641, 29.516, 29.319, 29.220, 25.095, 19.975; CH$_3$, 16.885, 14.258.

Prior to film preparation, the bis(2-methylpentyl)octadecanedioate (5.48 g) was purified using basic alumina (3.59 g). The basic alumina was added to a 0.5-inch column, and the bis(2-methylpentyl)octadecanedioate was added atop the alumina and allowed to pass through the alumina. Nitrogen pressure was added to assist in the speed of purification. The purified plasticizer was incorporated in PVB films, below.

Polyvinyl butyral (PVB) films were prepared using varying amounts of purified bis(2-methylpentyl)octadecanedioate ranging from none to 30 percent by weight of the plasticizer, relative to the total weight of the polymer composition. Table 2 shows the glass transition temperature (T$_g$) for films of varying amount of plasticizer incorporation.

TABLE 2

| Plasticizer Loading (wt %) | T$_g$ (° C.) |
|---|---|
| 0 | 76.0 |
| 10 | 61.7 |
| 20 | 51.4 |
| 30 | 51.8 |

Example 3

Bis(tri(ethylene glycol) monomethyl ether) Octadecanedioate

Dimethyl 1,18-octadecanedioate (ODDAME, 20.00 g), triethylene glycol monomethyl ether (23.97 g), and a stir bar were added to an oven dried, 250-mL three-necked round-bottom flask. A reflux condenser was placed in the middle neck, a septum was placed in the right-hand neck, and a glass stopper was placed in the left-hand neck. The reflux condenser was in line with a chilled collection flask for excess methanol, and this was in line with a water bubbler. A thermocouple and N$_2$ needle were inserted, and a light N$_2$ flow was maintained over the course of the reaction. Tin(II) 2-ethylhexanoate was added under a positive N$_2$ flow, the system was inerted, and the temperature was raised to 160° C. The reaction proceeded for over 4 hours, at which point the reaction was removed from heat, and a nitrogen sparge occurred over 1 hour. The material was allowed to cool to 40° C. prior to removal from apparatus; the product was stored under nitrogen. A light beige solid was recovered. The product was analyzed by $^1$H and $^{13}$C NMR. Analysis by $^1$H NMR provided the following chemical shifts: (400 MHz, CDCl$_3$) δ 0.85-0.92 (m), 1.20-1.40 (d), 1.57-1.68 (m), 2.34-2.28 (m), 3.37-3.45 (m), 3.54-3.57 (m), 3.60-3.79 (m), 4.19-4.25 (m). Analysis by $^{13}$C NMR provided the following chemical shifts: (400 MHz, CDCl$_3$) δ C, 173.619; CH, 34.049; CH2, 71.800, 70.478, 70.438, 69.058, 63.202, 58.877, 29.527, 29.510, 29.469, 29.330, 29.139, 28.994; CH3, 24.773.

Prior to film preparation, the bis(triethylene glycol monomethyl ether)octadecanedioate was purified using basic alumina. The basic alumina was added to a 0.5-inch column, and the bis(triethylene glycol monomethyl ether) octadecanedioate was added atop the alumina and allowed to pass through the alumina. Nitrogen pressure was added to assist in the speed of purification. The purified plasticizer was incorporated in PVB films, below.

Polyvinyl butyral (PVB) films were prepared using varying amounts of purified bis(triethylene glycol monomethyl ether)octadecanedioate ranging from none to 30 percent by weight of the plasticizer, relative to the total weight of the polymer composition. Table 3 shows the glass transition temperature (T$_g$) for films of varying amount of plasticizer incorporation.

TABLE 3

| Plasticizer Loading (wt %) | T$_g$ (° C.) |
|---|---|
| 0 | 76.0 |
| 10 | 55.4 |
| 20 | 42.2 |
| 30 | 30.5 |

Example 4

Bis(poly(ethylene glycol) monomethyl ether) Octadecanedioate

Dimethyl 1,18-octadecanedioate (ODDAME, 25.00 g), poly(ethylene glycol)methyl ether (avg. M$_n$=550, 100 g), and a stir bar were added to a 250-mL three-necked round-bottom flask. A chilled distillation head (5° C.) was attached, in line with primary and secondary collection flasks, out to a bubbler. The collection flasks were both on dry ice, and the system was inerted via a slow N$_2$ sparge. The temperature was raised to 55° C. with stirring, and the tin(II) 2-ethylhexanoate (0.58 g) was added. The temperature was raised to 140° C. and allowed to react for 1.25 hours. The temperature was then raised to 130° C. and allowed to react for 4 hours. The temperature was then raised once more, to 150° C. This was allowed to react for 1 hour at which point the heat was removed, and the product was allowed to cool with stirring. The product was stored overnight, under N$_2$. The reaction was resumed under the same conditions: 150° C., stirring, light nitrogen flow. The temperature was increased to 155° C., and the reaction was run another 6 hours. The product was cooled, and again stored under nitrogen. Tin(II) 2-ethylhexanoate (0.5578 g) was added to the reaction, and the reaction was resumed and run for another 6 hours. The product was cooled, and again stored under nitrogen. The reaction was resumed and tin(II) 2-ethylhexanoate (0.8560 g) was again added. The reaction ran at 160° C. for another 5 hours. The reaction mixture was then dosed with tin(II) 2-ethylhexanote (0.8578 g) and allowed to react at 165° C. for another 7 hours. The product was cooled with stirring, transferred to vials for storage, and stored under nitrogen. The product was analyzed by $^1$H and $^{13}$C NMR. Analysis by $^1$H NMR provided the following chemical shifts: (400 MHz, CDCl$_3$) δ 0.88-0.91 (m), 1.20-1.35 (d), 1.57-1.68 (m), 2.17 (s), 2.30-2.34 (td), 3.38 (s), 3.54-3.56 (m), 3.56-3.74 (m), 4.21-4.23 (t). Analysis by $^{13}$C NMR provided the following chemical shifts: (400 MHz, CDCl$_3$) δ C, 173.629; CH, 34.031; CH2, 77.489, 77.169, 76.849, 72.401, 71.774, 70.422, 70.361, 70.201, 69.037, 63.194, 58.882, 29.514, 29.497, 29.454, 29.316, 29.1330, 28.975; CH3, 24.749.

Prior to film preparation, the bis(poly(ethylene glycol) monomethyl ether)octadecanedioate was purified using basic alumina. The basic alumina was added to a 0.5-inch column, and the bis(poly(ethylene glycol)monomethyl ether)octadecanedioate was added atop the alumina and allowed to pass through the alumina. Nitrogen pressure was added to assist in the speed of purification. The purified plasticizer was incorporated in PVB films, below.

Polyvinyl butyral (PVB) films were prepared using varying amounts of purified bis(poly(ethylene glycol)monomethyl ether)octadecanedioate ranging from none to 40 percent by weight of the plasticizer, relative to the total weight of the polymer composition. Table 4 shows the glass transition temperature ($T_g$) for films of varying amount of plasticizer incorporation.

TABLE 4

| Plasticizer Loading (wt %) | $T_g$ (° C.) |
|---|---|
| 0 | 76.0 |
| 10 | 55.1 |
| 20 | 40.4 |
| 30 | 29.6 |
| 40 | p.s. |

*p.s. = phase separation

What is claimed is:

1. A compound of formula (I):

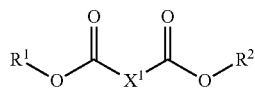

(I)

wherein:
X$^1$ is —(CH$_2$)$_{16}$—;
R$^1$ is 2-methylpentyl, 2-ethylhexyl, 2-butyloctyl, or 3-methylbutyl;
R$^2$ is a branched or unbranched C$_{4-24}$ alkyl, a branched or unbranched C$_{4-24}$ alkenyl, a branched or unbranched C$_{4-30}$ oxyalkyl, or a branched or unbranched C$_{4-30}$ oxyalkenyl, each of which is optionally substituted by one or more substituents selected independently from R$^3$;
R$^3$ is a halogen atom, —OH, —NH$_2$, C$_{1-6}$ alkyl, C$_{1-6}$ heteroalkyl, C$_{2-6}$ alkenyl, or C$_{2-6}$ heteroalkenyl.

2. The compound of claim 1, wherein R$^2$ is a branched C$_{4-20}$ alkyl, a branched C$_{4-20}$ alkenyl, a branched C$_{4-20}$ oxyalkyl, or a branched C$_{4-20}$ oxyalkenyl, each of which is optionally substituted by one or more substituents selected independently from R$^3$.

3. The compound of claim 2, wherein R$^2$ is a branched C$_{4-20}$ alkyl, which comprises branching at the 2-position of the alkyl moiety.

4. The compound of claim 2, wherein R$^2$ is a branched C$_{4-20}$ alkyl, which comprises branching at the 3-position of the alkyl moiety.

5. The compound of claim 3, wherein R$^2$ is a branched C$_{4-20}$ alkyl, which has no branching at the 1-position of the alkyl moiety.

6. The compound of claim 2, wherein R$^2$ is 2-methylpentyl, 2-ethylhexyl, 2-butyloctyl, or 3-methylbutyl.

7. The compound of claim 1, wherein R$^2$ is branched or unbranched C$_{4-30}$ oxyalkyl, which is optionally substituted by one or more substituents selected independently from R$^3$.

8. The compound of claim 7, wherein R$^2$ is —(CH$_2$—CH$_2$—O)$_{1-12}$—(C$_{1-6}$ unbranched alkyl).

9. The compound of claim 8, wherein R$^2$ is —CH$_2$—CH$_2$—O—CH$_3$, —(CH$_2$—CH$_2$—O)$_2$—CH$_3$, —(CH$_2$—CH$_2$—O)$_3$—CH$_3$, —(CH$_2$—CH$_2$—O)$_4$—CH$_3$, —(CH$_2$—CH$_2$—O)$_5$—CH$_3$, —(CH$_2$—CH$_2$—O)$_6$—CH$_3$, —(CH$_2$—CH$_2$—O)$_7$—CH$_3$, —(CH$_2$—CH$_2$—O)$_8$—CH$_3$, —(CH$_2$—CH$_2$—O)$_9$—CH$_3$, —(CH$_2$—CH$_2$—O)$_{10}$—CH$_3$, —(CH$_2$—CH$_2$—O)$_{11}$—CH$_3$, or —(CH$_2$—CH$_2$—O)$_{12}$—CH$_2$—CH$_3$.

* * * * *